United States Patent
Thramann (12)

(10) Patent No.: US 6,689,097 B2
(45) Date of Patent: Feb. 10, 2004

(54) FLOW-BY CHANNEL CATHETER AND METHOD OF USE

(76) Inventor: Jeffrey J. Thramann, 13203 N. 14th Way, Phoenix, AZ (US) 85022

(*) Notice: Subject to any disclaimer, the term of this patent is extended or adjusted under 35 U.S.C. 154(b) by 0 days.

(21) Appl. No.: 10/279,349

(22) Filed: Oct. 24, 2002

(65) Prior Publication Data

US 2003/0050599 A1 Mar. 13, 2003

Related U.S. Application Data

(63) Continuation of application No. 09/501,416, filed on Feb. 9, 2000, now Pat. No. 6,482,172.

(51) Int. Cl.[7] .............................................. A61M 29/00
(52) U.S. Cl. .................. 604/96.01; 604/97.02; 604/101.01; 604/101.05; 604/919; 604/101.04
(58) Field of Search ........................ 604/96.01, 97.01, 604/97.02, 99.01, 101.01, 101.05, 164.13, 523, 915, 919, 920, 101.04, 104; 606/191, 194, 195

(56) References Cited

U.S. PATENT DOCUMENTS

| | | |
|---|---|---|
| 4,411,055 A | 10/1983 | Simpson et al. |
| 4,456,000 A | 6/1984 | Schjeldahl et al. |
| 4,838,268 A | 6/1989 | Keith et al. |
| 4,848,344 A | 7/1989 | Sos et al. |
| 4,909,252 A | 3/1990 | Goldberger |
| 4,946,466 A | 8/1990 | Pinchuk et al. |
| 4,983,167 A | 1/1991 | Sahots |
| 5,000,743 A | 3/1991 | Patel |
| 5,019,042 A | 5/1991 | Sahota |
| 5,090,958 A | 2/1992 | Sahota |
| 5,125,896 A | 6/1992 | Hojeibane |
| 5,147,377 A | 9/1992 | Sahota |
| 5,160,321 A | 11/1992 | Sahota |

(List continued on next page.)

FOREIGN PATENT DOCUMENTS

| | | |
|---|---|---|
| DE | 0 306 010 | 8/1989 |
| DE | 0 361 314 | 4/1990 |

*Primary Examiner*—Sang Y. Paik
*Assistant Examiner*—Fadi H. Dahbour
(74) *Attorney, Agent, or Firm*—Cook, Alex, McFarron, Manzo, Cummings & Mehler, Ltd.

(57) ABSTRACT

A vascular catheter assembly includes an over-the-wire stent deployment catheter and a flow-by-channel assembly. The stent deployment catheter is positioned just below the occluded artery in accordance with standard procedures. The flow-by-channel then shunts blood, and thus all friable plaque, from the high pressure carotid occlusion to the negative pressure extremity to effectively reverse the flow of blood through the occluded artery. The stent is then advanced into the narrowed artery and deployed. Thus, the vascular catheter assembly takes advantage of the collateral blood flow to solve the problem of stroke during endovascular procedures.

1 Claim, 7 Drawing Sheets

U.S. PATENT DOCUMENTS

| | | |
|---|---|---|
| 5,181,911 A | 1/1993 | Shturman |
| 5,226,889 A | 7/1993 | Sheiban |
| 5,261,878 A | 11/1993 | Galindo |
| 5,277,199 A | 1/1994 | DuBois |
| 5,320,605 A | 6/1994 | Sahota |
| 5,458,574 A | 10/1995 | Machold |
| 5,489,270 A | 2/1996 | van Erp |
| 5,558,642 A * | 9/1996 | Schweich, Jr. et al. . 604/101.05 |
| 5,611,812 A | 3/1997 | Skornia |
| 5,716,340 A | 2/1998 | Schweich, Jr. et al. |
| 5,725,535 A | 3/1998 | Hegde et al. |
| 5,868,708 A * | 2/1999 | Hart et al. ............. 604/101.05 |
| 5,893,841 A | 4/1999 | Glickman |
| 5,919,163 A * | 7/1999 | Glickman .............. 604/101.05 |
| 5,951,514 A | 9/1999 | Sahuta |
| 5,964,778 A | 10/1999 | Fugoso et al. |
| 5,968,069 A | 10/1999 | Dusbabek et al. |
| 6,022,336 A * | 2/2000 | Zadno-Azizi et al. .. 604/101.05 |
| 6,066,156 A | 5/2000 | Yan |
| 6,099,497 A | 8/2000 | Adams et al. |
| 6,126,635 A * | 10/2000 | Simpson et al. ........ 604/101.05 |
| 6,139,517 A * | 10/2000 | Macoviak et al. ....... 604/96.01 |
| 6,143,015 A | 11/2000 | Nobles |
| 6,148,825 A | 11/2000 | Anderson et al. |
| 6,156,005 A | 12/2000 | Theron |
| 6,159,219 A | 12/2000 | Ren |
| 6,159,229 A | 12/2000 | Jendersee et al. |
| 6,206,262 B1 | 3/2001 | Achelpohl et al. |
| 6,221,043 B1 | 4/2001 | Fishell et al. |
| 6,228,110 B1 | 5/2001 | Munsinger |
| 6,234,995 B1 * | 5/2001 | Peacock, III ............. 604/96.01 |
| 6,248,086 B1 * | 6/2001 | Sweezer et al. ......... 604/97.02 |
| 6,254,563 B1 * | 7/2001 | Macoviak et al. ...... 604/101.05 |
| 6,290,689 B1 | 9/2001 | Delaney et al. |
| 6,423,032 B2 | 7/2002 | Parodi |
| 6,443,912 B1 | 9/2002 | Mazzola et al. |
| 2001/0056285 A1 | 12/2001 | Dutta et al. |
| 2002/0087119 A1 | 7/2002 | Parodi |

\* cited by examiner

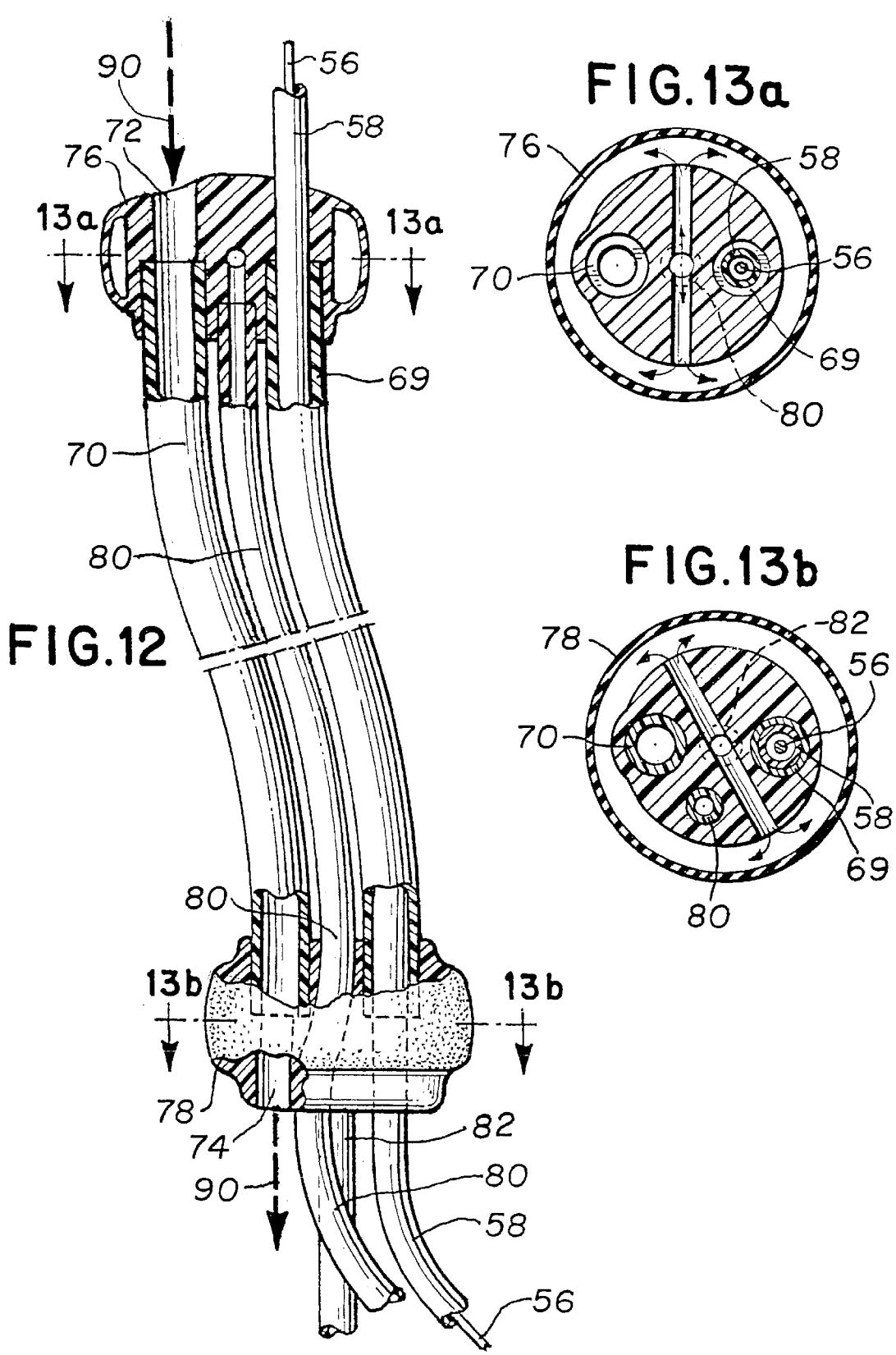

FLOW-BY CHANNEL CATHETER AND METHOD OF USE

This is a continuation of U.S. patent application Ser. No. 09/501,416, filed Feb. 9, 2000. now U.S. Pat. No. 6,482,172.

BACKGROUND OF THE INVENTION

The present invention relates generally to a device and method for the treatment of atherosclerotic disease, and more particularly, to a device and method which utilizes the collateral blood flow of the Circle of Willis to aid in the extracting of an obstructed vessel supplying blood to the brain.

Atherosclerotic disease of the internal carotid artery is the most common reason for stroke. Atherosclerotic plaques form on the inner lining of the blood vessels supplying blood to the brain, and over time enlarge and become friable. Typically, a stroke occurs when small flecks of plaque break loose, travel with the blood into the brain, and lodge in an end vessel. By lodging in an end vessel, the clot prevents blood from passing through to the brain tissue supplied by the vessel. Without blood, the brain tissue will die within minutes.

Most flecks of plaque that result in clots spontaneously breakdown and cause only a temporary occlusion of blood, and thus reversible symptoms. This is termed a Transient ischemic Attack (TIA) and is a warning for an impending stroke. Because of the warning provided by a TIA, numerous patients are identified each year prior to a full stroke. Once identified, either because of a TIA or other symptoms, patients typically undergo a traditional surgical removal of the plaque. This procedure is termed a Carotid Endarterectomy (CEA) and basically involves opening the internal carotid artery, removing the plaque, and closing the vessel with suture. In order to open the internal carotid artery without the patient bleeding to death, the internal carotid artery must be clamped. While the vessel is clamped, the patient will be dependant on collateral blood flow from the other three vessels supplying blood to the brain, and an open Circle of Willis, to get blood to the part of the brain usually supplied by the clamped artery.

As with any major surgical procedure, there exists a certain amount of inherent risk to the patient. However, the major risk of a CEA is, ironically, a stroke because of the small microscopic flecks of plaque that remain in the vessel. The problems arising from the surgical intervention of a CEA have created strategies to repair the narrowing of the carotid artery without such surgical intervention. One such strategy involves the use of catheters to deploy stents that open the vessel and plaster the plaque against the vessel wall. Although such a procedure is significant in that the patient does not require surgery or general anesthesia, again the major risk therein is a high stroke rate. This happens due to the catheter and stent breaking off pieces of the friable plaque which are then carried directly into the brain.

In view of the aforementioned needs and the shortcomings of the prior art, it is therefore an object of the present invention to provide a system which overcomes the deficiencies of the current practices whereby a device and method is provided for the treatment of atherosclerotic disease.

Accordingly, it is a general object of the present invention to provide a new and improved catheter device and method.

It is a more specific object of the present invention to provide a device and method for the extracting of an obstructed vessel without surgical intervention.

Yet a more specific object of the present invention is to provide a catheter device and method which utilizes the collateral blood flow of the Circle of Willis to aid in the extricating of the obstructed vessel supplying blood to the brain to help prevent stroke.

SUMMARY OF THE INVENTION

The invention is directed to a vascular catheter assembly comprising an elongated tubular catheter body having an inner lumen to receive a guide wire and an expandable member near its end. A channel member having expandable members near both ends is slidably engaged to the catheter and includes a passageway defining an inner channel lumen.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 12 is a side view of the flow-by channel assembly of FIG. 11.

FIG. 13a is a cross-sectioned view of the distal occlusion balloon taken along lines 13a—13a of FIG. 12.

FIG. 13b is a cross-sectioned view of the proximal occlusion balloon taken along lines 13b—13b of FIG. 12.

DESCRIPTION OF THE PREFERRED EMBODIMENT

Figure 1:
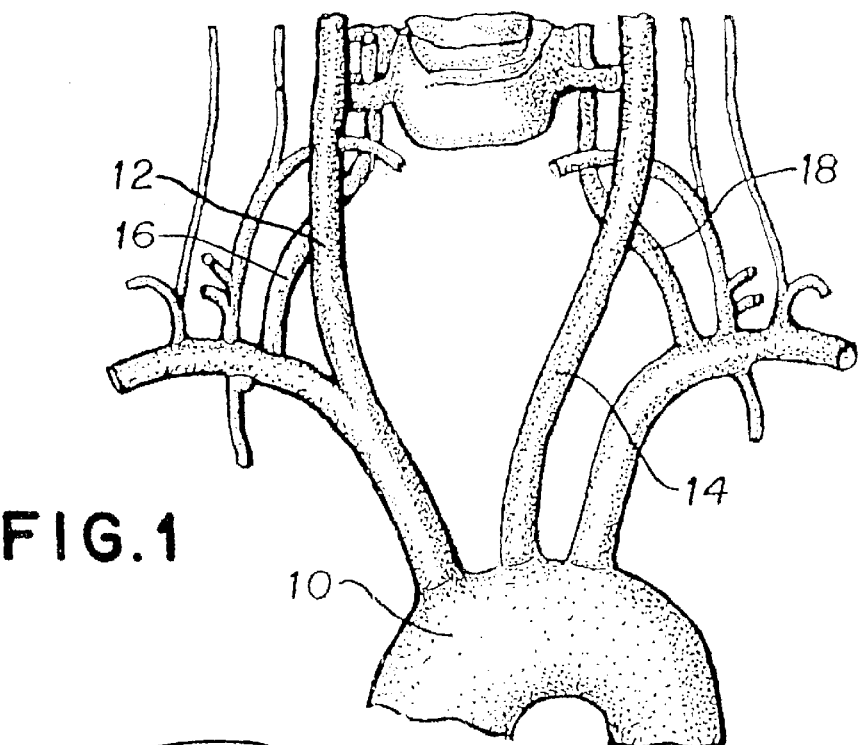
FIG. 1 is a front view of the origins of the common carotid and vertebral arteries stemming from the heart.
Figure 2:
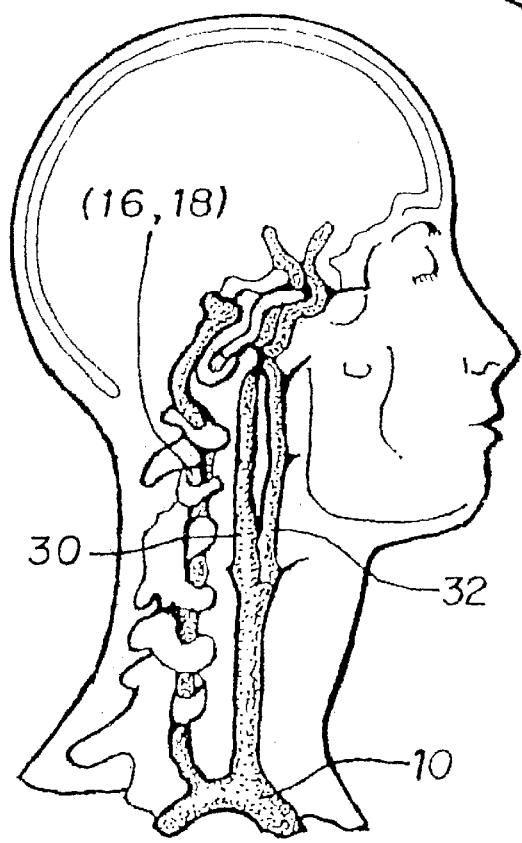
FIG. 2 is a side view of the cervical carotid and vertebral arteries as they enter the brain.
Figure 3:
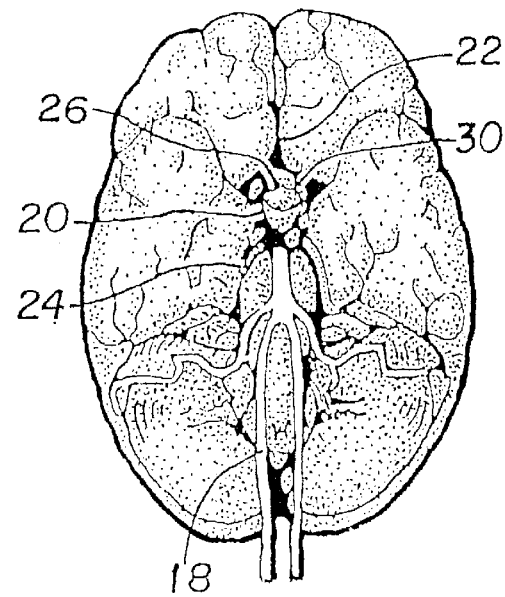
FIG. 3 is a bottom view of the base of the brain showing the key collateral circulation of the Circle of Willis.

In order to fully appreciate the operation and value of the present invention, a more detailed look at the arterial system, occlusions thereof, and the deficiencies of current practices to remedy these occasions is needed. Referring to the figures, and particularly to FIG. 1, the aortic arch 10 supplies blood to the four major arteries that supply blood to the brain. In particular, there are two in the front of the neck, the right common carotid 12 and the left common carotid 14, and two in the back of the neck, the right vertebral 16 and the left vertebral 18.

At the base of the brain, all four of these arteries are joined through connecting vessels to form a circle termed The Circle of Willis, which is a vascular structure located on the floor of the cranial cavity. The Circle of Willis is the key collateral pathway connecting both carotid arteries with the circulation at the base of the brain. This circle includes the posterior communicating arteries 20, the proximal anterior cerebral 22 and posterior cerebral arteries 24, and the anterior communicating artery 26. Because this loop is supplied by multiple vessels, in an arrangement which provides collateral flow, damage to any one vessel will not compromise the blood supply to the brain.

The right common carotid artery 12 arises from the brachiocephalic trunk 28 which arises from the aortic arch 10. Each common carotid bifurcates into an internal 30 and external 32 component, see FIG. 4. The external carotid 32 supplies blood to the face and does not play a role in stroke, while the internal carotid 30 has no branches and feeds directly into the brain.

Figure 4:
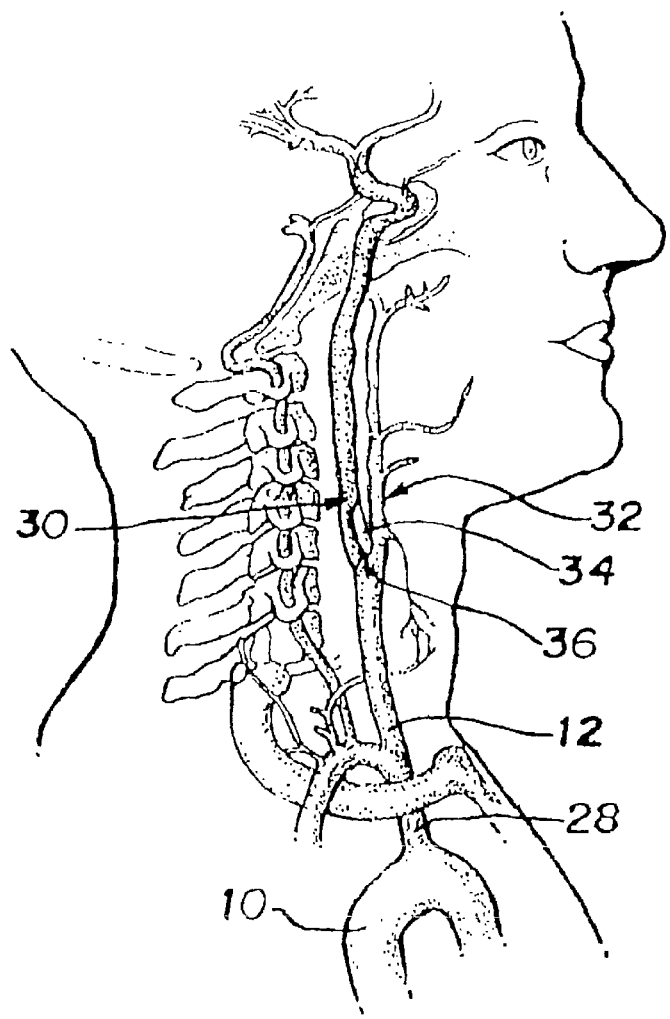
FIG. 4 is a side view cut away section of the internal carotid artery showing stenosis or occlusion thereof.

Typically, a stroke occurs when the internal carotid artery 30 becomes clogged or ruptures with the formation of atherosclerotic plaque on the inner lining thereof being most common, see FIG. 4. This buildup of plaque 34 most frequently occurs just after the bifurcation point 36 of the common carotid 12 into internal 30 and external 32 carotid. Such a buildup of FIG. 4 is better illustrated by the enlarged view of the inner lining as shown in FIG. 5.

Figure 5:
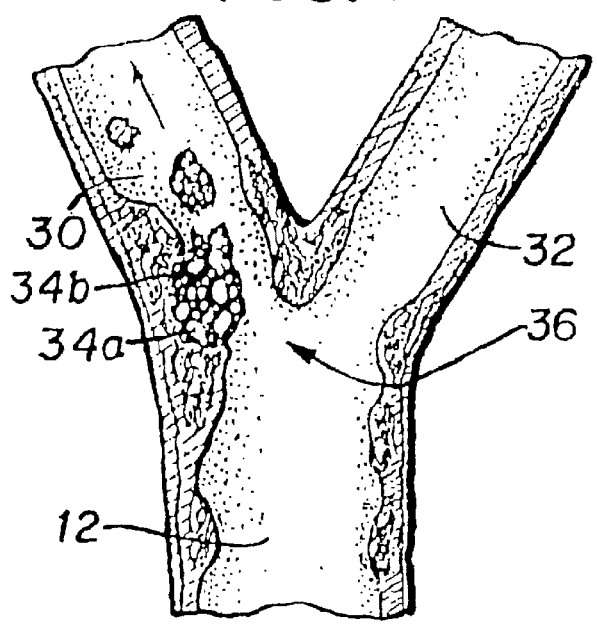
FIG. 5 is an enlarged view of the inner lining blood vessel showing friable plaque.
Figure 6:
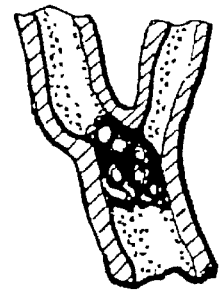
FIG. 6 is an enlarged view of a portion of the arterial tree distal to the vessel of FIG. 5.

FIG. 5 shows the atherosclerotic plaque 34 buildup at the point 36 of the arterial bifurcation. The initial buildup 34a is illustrated in a light shade while the more friable buildup 34b is a darker shade. The plaque may eventually cause total arterial occlusion of the internal carotid, or as depicted in FIGS. 5 and 6, may break loose and occlude blood vessels distally in the arterial tree (FIG. 6). The later, as it will be past the Circle of Willis, causing stroke and irreversible damage to brain cells.

Figure 7:
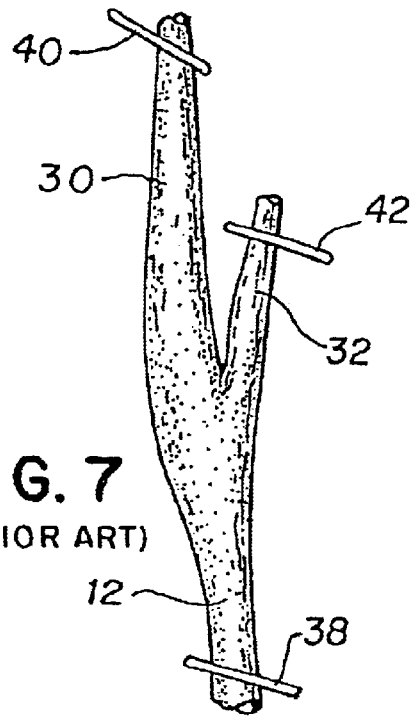
FIG. 7 is an enlarged view of the clamped vessels during the beginning of a Carotid Endarterectomy procedure.
Figure 8:
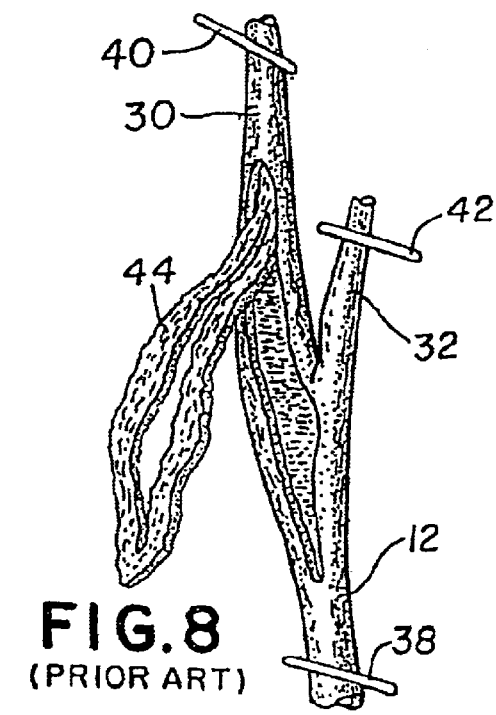
FIG. 8 is an enlarged view of the clamped vessels during the removal of plaque phase of a Carotid Endarterectomy procedure.

The prior art procedure for removing this buildup is called a Carotid Endarterectomy (CEA) and involves the clamping of the arteries, removing the plaque, and closing the vessel with suture. This CEA procedure is very simplistically illustrated by FIGS. 7 and 8, but in fact is quite complex. In order to clamp the internal carotid artery, you cannot simply put a clamp across the vessel like you could with a water hose. The reason for this is because of the collateral blood flow through the Circle of Willis. If a single clamp were placed across the internal carotid artery, blood traveling up the artery to the brain would be stopped at the level of the clamp while blood traveling up the other three vessels to the brain would continue. Since fluids will travel along the path of least resistance, the blood traveling up the other three vessels would enter the Circle of Willis, notice the low pressure in the clamped vessel and travel back down the empty portion of the clamped vessel. Note that this flow from the Circle of Willis would only occur if the vessel were opened.

Because of this collateral blood flow, surgeons need three clamps to occlude blood flow through the internal carotid artery 30. A clamp 38 is placed across the carotid artery 12 before it divides into the internal 30 and external 32 carotid artery. This clamp 38 will prevent blood flow up towards the brain. Another clamp 40 is placed on the internal carotid artery 30 above the plaque. This clamp 40 prevents flow back down from the brain. Yet another clamp 42 is placed on the external carotid artery 32. This clamp 42 prevents blood from flowing down the external carotid from the face.

An elegant surgical strategy that takes advantage of collateral blood flow through the Circle of Willis has been developed to keep the risk of a stroke during a CEA low. During the CEA procedure, when the artery is clamped and the plaque removed (44, FIG. 8), small microscopic flecks of plaque inevitably remain in the vessel. These flecks cannot be manually removed by the surgeon, yet they could cause vessel obstruction and subsequent stroke if they were allowed to enter the circulation. To prevent this, surgeons remove the clamps in a precise order, and under tight control, while the artery is still open. The clamp 40 on the internal carotid artery 30 is removed first. This enables blood coming through the Circle of Willis to rush down the internal carotid artery and out of the opened blood vessel. This effectively washes any small flecks of plaque out of the artery. The clamp 40 is then reapplied after a few seconds. This is then repeated with the external carotid artery and clamp 42. Once all the flecks have been washed out, the vessel is closed with suture and all clamps removed to allow blood to once again flow forward into the brain.

Figure 9:
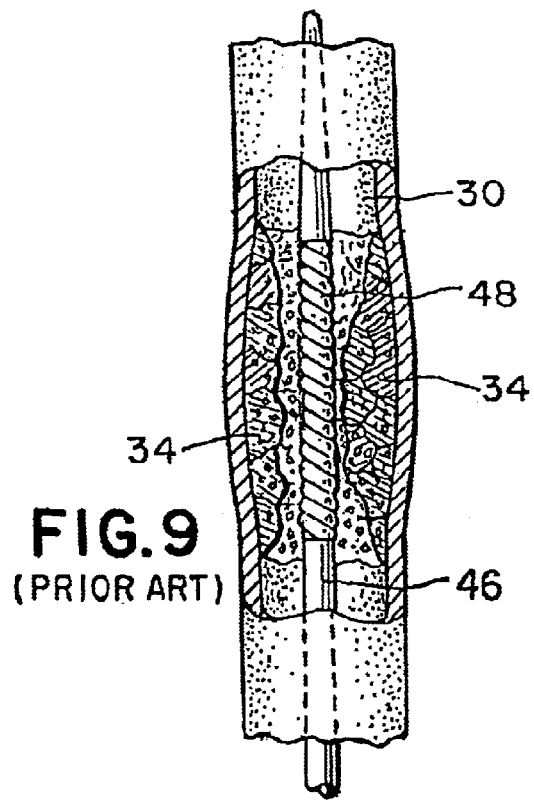
FIG. 9 is an enlarged view of the inner lining of a blood vessel having a plaque buildup during a stent insertion procedure.
Figure 10:
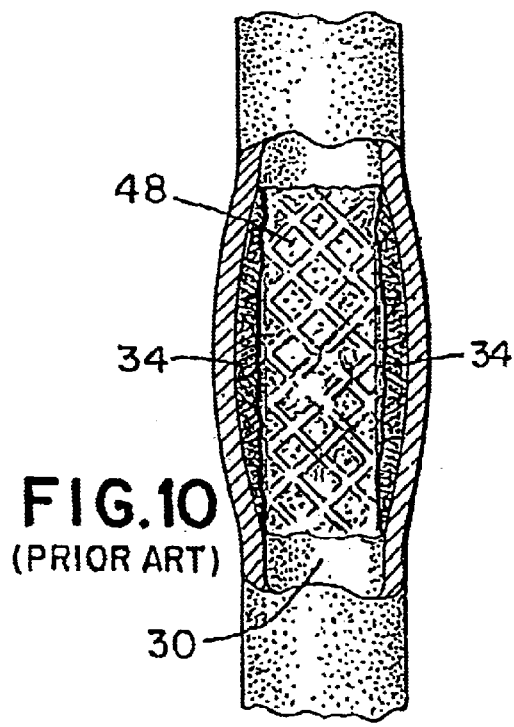
FIG. 10 is an enlarged view of the inner lining of the blood vessel of FIG. 9 showing the deployed stent.

A more recent prior art procedure repairs the narrowing of the internal carotid artery without surgical intervention. The main strategy of this procedure involves the use of catheters and is illustrated in FIGS. 9 and 10. The catheters 46 are inserted into an easily accessible blood vessel in the arm or groin and then steered into the internal carotid artery 30 where they are utilized to deploy stents 48 that open the vessel and plaster the plaque 34 against the vessel wall. However, the major problem with this endovascular technique is, once again, a stroke. This is due to the catheter causing pieces of the friable plaque to break off as it is passed through the narrowed portion of the vessel caused by the plaque. Since there are no clamps, the blood carries the flecks of plaque directly into the brain. Additionally, when the stent is deployed to plaster the plaque up against the vessel wall, more pieces of the plaque are broken off.

Figure 11:
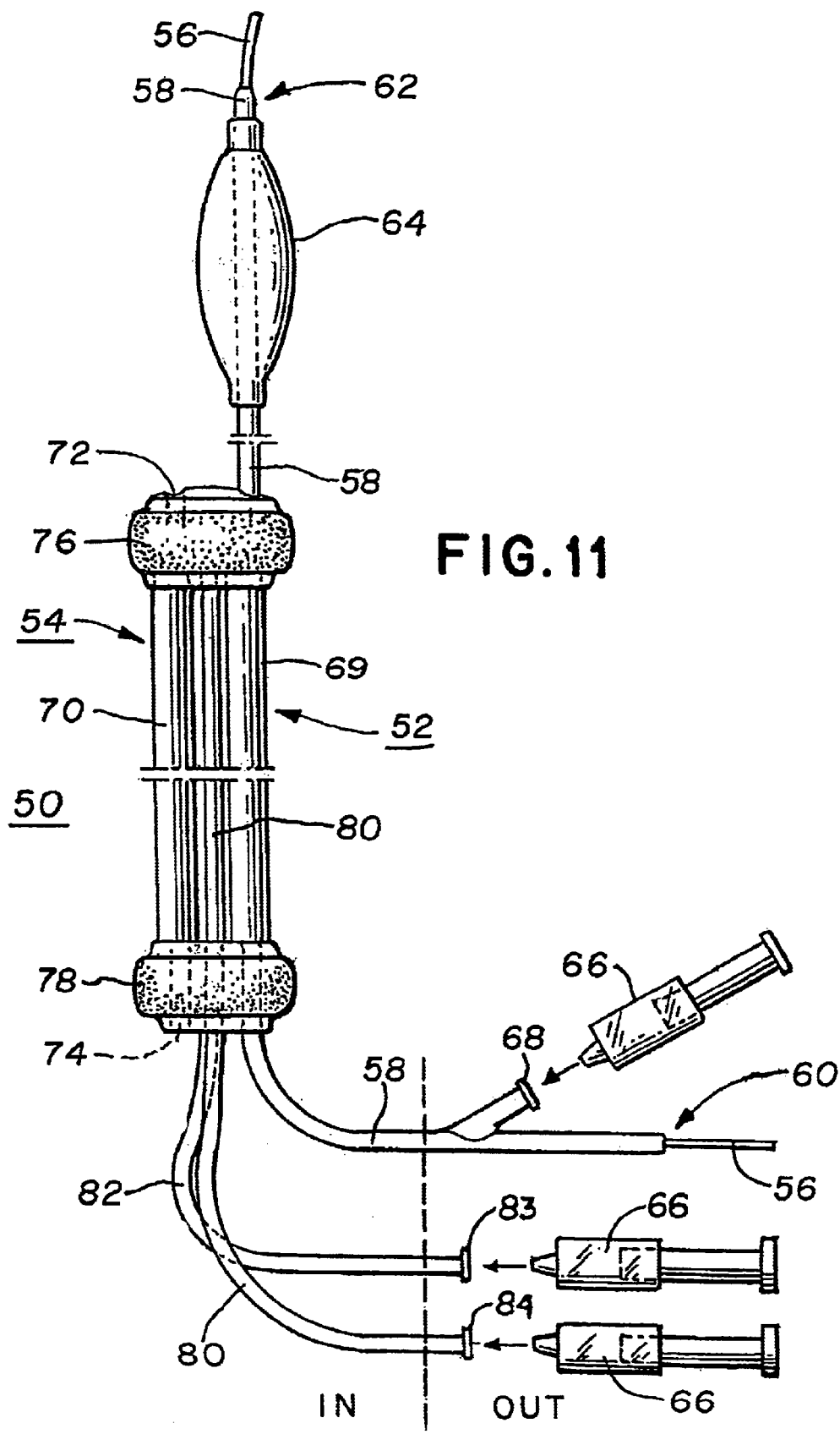
FIG. 11 is a side view of the flow-by channel catheter assembly and system constructed in accordance with the principles of the present invention.

The present invention is both a combination of these two prior art procedures as well as a novel approach to solve the atherosclerotic disease problem. More particularly, the present invention takes advantage of the collateral blood flow to completely solve the problem of stroke during endovascular procedures. Referring to FIG. 11, the preferred embodiment of the catheter assembly 50 is shown. This system basically consists of an over-the-wire stent deployment catheter assembly 52 and a flow-by-channel assembly 54. The design and structure of the over-the-wire stent deployment catheter assembly 52 to be used with the present invention may be better described in U.S. Pat. No. 5,782,855, incorporated herein by reference. However, for illustration purposes a simplified description of the over-the-wire stent deployment catheter assembly 52 includes a guide wire 56 and catheter 58 having proximal 60 and distal 62 ends defining an inner lumen extending therebetween and providing respective guide wire openings. Attached near the distal end of the catheter 58 is a stent deployment balloon 64 used to deploy a stent 48 as shown in the prior art FIGS. 9 and 10. This deployment balloon 64 is inflated and deflated through the use of an air syringe 66 or the like via the deployment balloon port 68.

The preferred embodiment of the flow-by-channel assembly 54 is attached to the catheter assembly 52 as shown in FIG. 11, but is better illustrated by the enlarged view of FIGS. 12 and 13. The flow-by-channel is attached via a sheath 69 around the over-the-wire catheter such that the over-the-wire catheter with the loaded stent can be adjusted for stent positioning without moving the flow-by-channel occlusion balloons which must remain stationary once inflated. This flow-by-channel assembly 54 includes a flow-by-channel 70 having a distal end 72 and a proximal end 74 defining an inner lumen therebetween. The assembly further includes a distal occlusion balloon 76 and a proximal occlusion balloon 78, and an air channel tube 80. The air channel tube 80 provides air to the distal occlusion balloon 76 and the flow-by-channel 70. Thus, via tube port 84, the distal occlusion balloon 76 and the flow-by-channel 70 are inflated and deflated through the use of an air syringe 66 or the like. Similarly, occlusion tube 82 provides air to the proximal occlusion balloon 78 via occlusion port 83 and, as discussed, is inflated and deflated through the use of an air syringe or the like.

Figure 14:
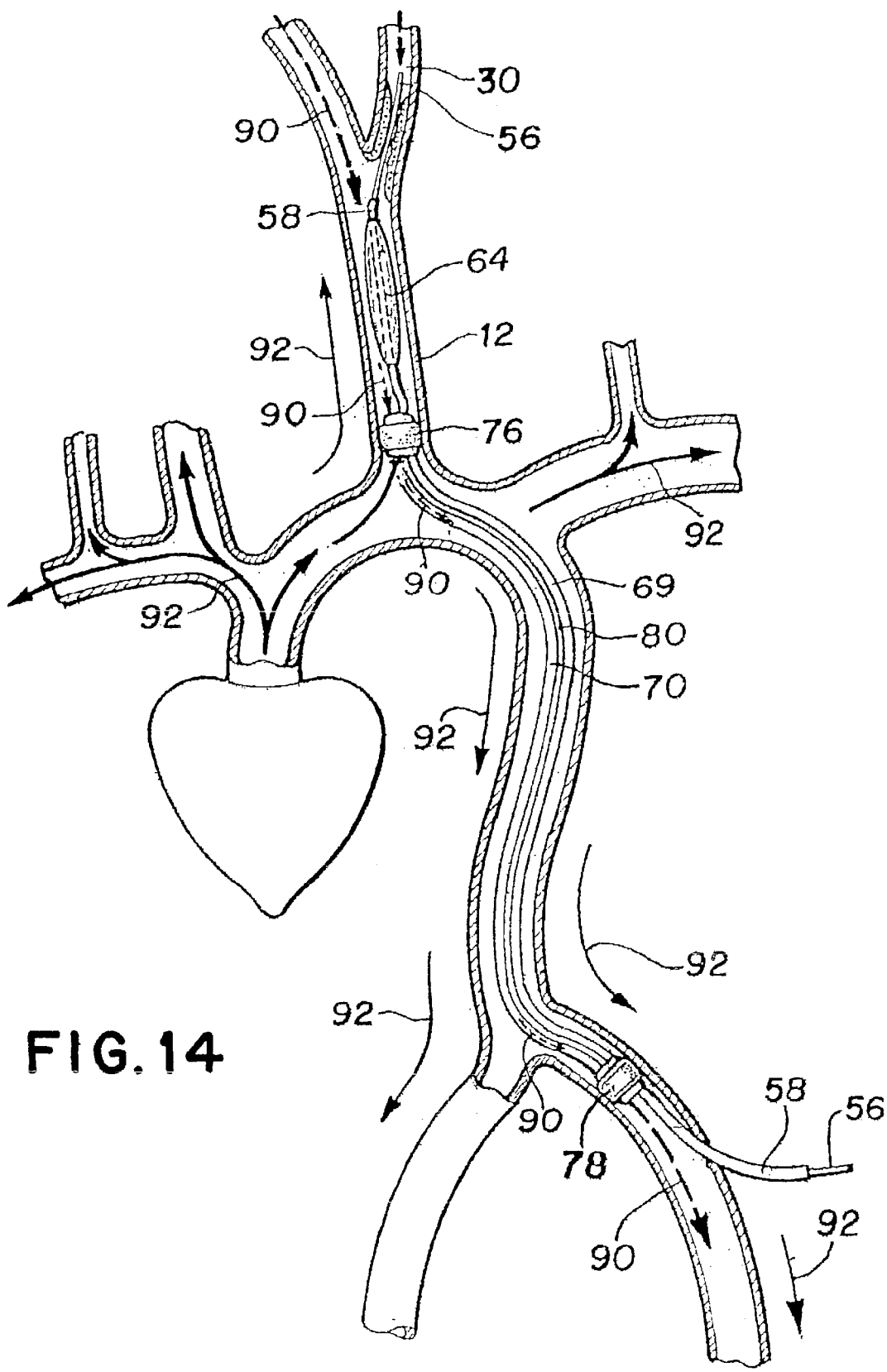
FIG. 14 is a side view of the flow-by channel and catheter assembly and system shown during use within the arterial walls.
Figure 15:
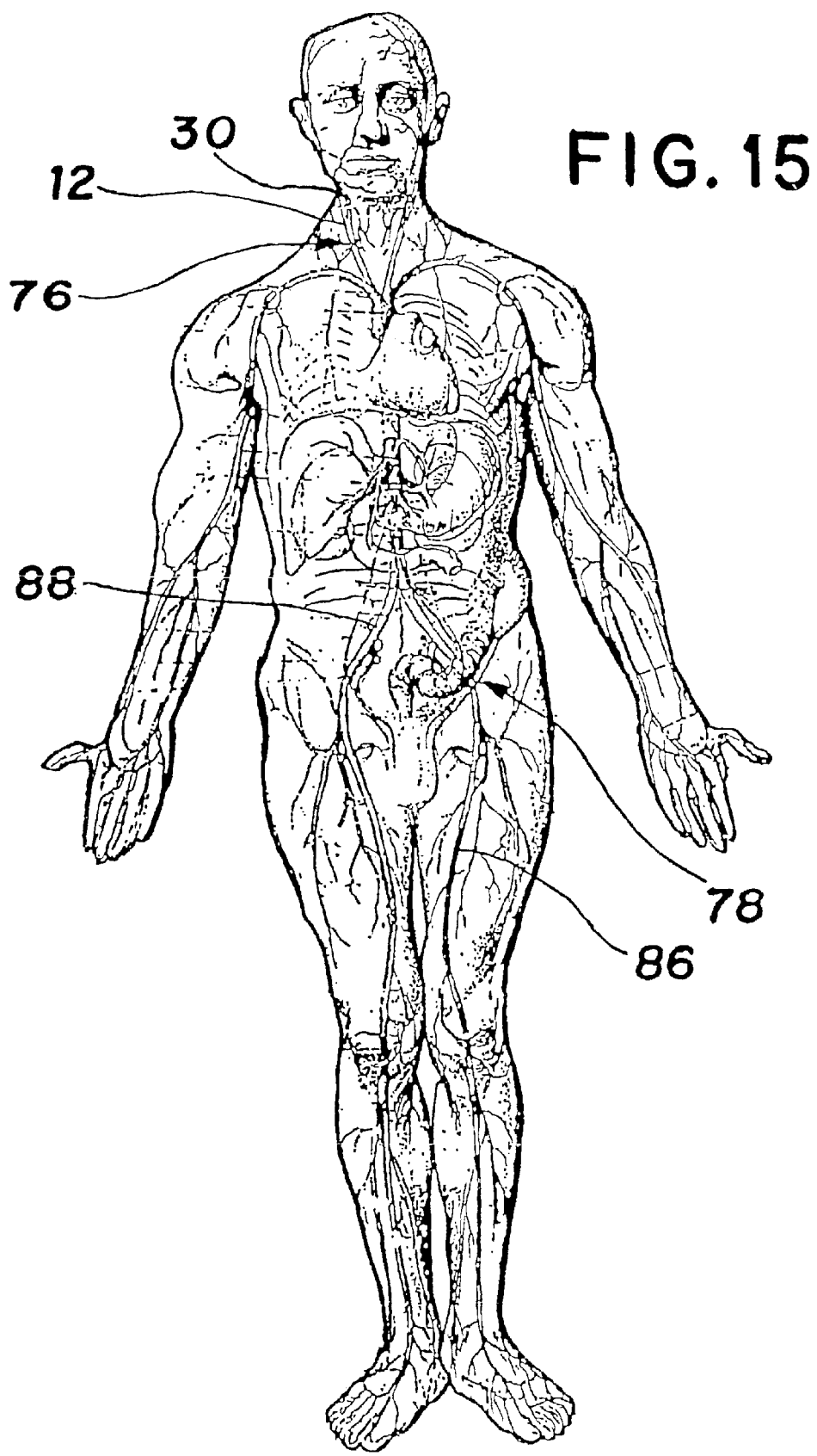
FIG. 15 is a front view of the systemic arteries of an adult male.

FIGS. 13 and 14 are shown to better illustrate the procedure utilizing the preferred embodiment of the present invention. The catheter assembly 50 is inserted into the femoral artery 86 in accordance with standard procedures. This includes placing of the guide wire 56 and inserting the catheter by placing it over the guide wire 56 with the stent preloaded. The catheter 50 is then steered up into the internal carotid artery 30. Once in position, the distal balloon 76 is expanded in the carotid artery 12 before it divides into the internal 30 and external 32 carotid arteries. This, in effect, blocks blood flow up the carotid artery 12 to the brain just like the clamp 38 during a CEA. Again, because of the Circle of Willis, blood will want to flow down the occluded vessel in a reverse direction. This works well during a CEA when the clamps are removed because the vessel is open and there is a strong negative pressure (least resistance) pulling the blood down from the Circle of Willis. In the endovascular case a negative pressure has to be created.

As the catheter 50 travels from the femoral artery 86 in the groin up to the carotid 12, it passes through the common iliac artery 88 in the lower abdomen. There are two common iliac arteries, a right and a left, and they are the sole suppliers of blood to their respective lower extremity. When the distal balloon 76 in the carotid artery 12 is expanded, the proximal balloon 78 in the common iliac 88 is also expanded. The expansion of proximal balloon 78 blocks blood flow to the leg (the leg can survive for hours without blood, so this is not critical) and subsequently creates a large negative pressure within the arterial vasculature of the leg.

Inflation of the balloons (76,78) needs to be variable and controlled by how much air is inserted. This variability is important because complete occlusion of the common iliac artery 88 in some patients may produce too much of a negative pressure resulting in blood being "stolen" from the brain to the leg. In these instances, the leg occlusion may only need to be 75% or the like. If this is the case, an alternate embodiment of the present invention may include separate air channels and thus separate deployment balloon parts. Also, as each patient and thus each procedure is different, an additional occlusion balloon may be necessary in the external carotid artery 32 (not shown). This additional external carotid artery balloon occlusion would keep the blood flow from being "stolen" or alternately an excessiveness of blood being supplied to the face.

In any event, the flow-by-channel 70 of the catheter then shunts blood from the high pressure carotid occlusion to the negative pressure leg. This effectively reverses the flow of blood through the internal carotid artery 30. Once blood flow is reversed (indicated by dashed arrows 90 rather than the solid arrows 92 representing normal blood flow) the stent is advanced into the narrowed internal carotid artery 30 and deployed via balloon 64. Any flecks of plaque that are broken off are washed through the flow-by-channel 70 where they are filtered out of circulation. After deployment of the stent and clearing of all plaque debris, the balloons are deflated and the catheter removed.

Thus, through the utilization of the present invention, an obstructed vessel leading to the brain is extracted without fear of a procedurally caused stroke. More particularly, the loose plaque that flows to the brain during a CEA and/or the common stent deploying catheter procedure is eliminated. Through the collateral blood flow of the Circle of Willis, this loose plaque is "reverse-flowed", by the present invention, into the leg. As this blood carrying any plaque is recirculated throughout the body, the plaque will break down before reaching the brain. Once again, as each patient requires a slightly different procedure, it may become necessary to aid in this filtration process. More particularly, an alternate embodiment of the present invention may include a flow-by-channel heaving an internal filtration process to ensure proper filtration. In any event, the present invention keeps this loose plaque from returning to the brain.

While particular embodiments of the invention have been shown and described, it will be obvious to those skilled in the art that changes and modifications may be made therein without departing from the invention in its broader aspects and, therefore, the aim in the appended claim is to cover all such changes and modifications as fall within the true spirit and scope of the invention.

What is claimed is:

1. An apparatus for removing plaque from an obstructed vessel, comprising:

a catheter having proximal and distal ends and a lumen extending therethrough, said distal end adapted to be disposed in a patient's carotid artery;

a channel member slidably positionable adjacent said catheter, said channel member having proximal and distal ends and a lumen extending therethrough, siad proximal end adapted to be disposed in a patient's femoral artery;

a first occlusion element disposed proximally adjacent said distal end of said channel member;

a second occlusion element disposed proximally adjacent said proximal end of said channel member; and said occlusion elements having a contracted state for transluminal insertion and an expanded state wherein the occlusion elements occlude antegrade flow in the vessel.

* * * * *